US008747935B2

(12) United States Patent
Villota et al.

(10) Patent No.: US 8,747,935 B2
(45) Date of Patent: Jun. 10, 2014

(54) NUTRITIONALLY ENHANCED PASTA

(75) Inventors: Ricardo Villota, Lake Zurich, IL (US); Guillermo Haro, Skokie, IL (US); Laura G. Hill, Prospect Heights, IL (US); Trevor A. Sweeney, Evanston, IL (US)

(73) Assignee: Kraft Foods Group Brands LLC, Northfield, IL (US)

( * ) Notice: Subject to any disclaimer, the term of this patent is extended or adjusted under 35 U.S.C. 154(b) by 0 days.

(21) Appl. No.: 13/229,409

(22) Filed: Sep. 9, 2011

(65) Prior Publication Data

US 2011/0318452 A1    Dec. 29, 2011

Related U.S. Application Data

(62) Division of application No. 11/319,149, filed on Dec. 27, 2005, now abandoned.

(51) Int. Cl.
*A23L 1/16* (2006.01)

(52) U.S. Cl.
USPC ............................ 426/557; 426/451; 426/516

(58) Field of Classification Search
USPC ......................................... 426/557, 451, 516
See application file for complete search history.

(56) References Cited

U.S. PATENT DOCUMENTS

| | | | |
|---|---|---|---|
| 3,615,677 | A | 10/1971 | Scharschmidt et al. |
| 3,949,101 | A | 4/1976 | Murthy |
| 3,968,258 | A | 7/1976 | Akin et al. |
| 4,120,989 | A | 10/1978 | Grindstaff et al. |
| 4,361,591 | A | 11/1982 | Taufiq |
| 4,508,825 | A * | 4/1985 | Kim et al. ............ 435/201 |
| 4,876,104 | A | 10/1989 | McGuire et al. |
| 5,063,072 | A * | 11/1991 | Gillmore et al. ...... 426/557 |
| 5,916,619 | A * | 6/1999 | Miyazaki et al. ..... 426/557 |
| 6,322,826 | B2 | 11/2001 | Zohoungbogbo |
| 6,326,049 | B1 | 12/2001 | Halden et al. |
| 6,569,483 | B2 | 5/2003 | Zohoungbogbo |
| 6,797,308 | B2 * | 9/2004 | Pasch et al. ........... 426/557 |
| 6,855,362 | B2 | 2/2005 | Brown et al. |
| 2002/0155206 | A1 | 10/2002 | Orlando |
| 2003/0091698 | A1 | 5/2003 | Marsland |
| 2006/0115567 | A1 * | 6/2006 | Hoegh ................. 426/557 |

FOREIGN PATENT DOCUMENTS

| | | |
|---|---|---|
| DE | 1 900 197 | 3/1971 |
| GB | 1 182 510 | 2/1970 |
| GB | 2 079 287 A | 1/1982 |
| WO | 99/57984 A1 | 11/1999 |
| WO | 01/05246 A2 | 1/2001 |
| WO | 01/64056 A1 | 9/2001 |

OTHER PUBLICATIONS

Li, R. S., Improved tofu food products and methods of manufacture, PCT Patent Application WO 99/03356 A1, 1999, Abstract, 1 page.
Ishijima, I., Wheat protein-improving agent, wheat protein food using the same agent and its production, Japanese Patent Application JP 8-173053 A, 1994, Abstract, 1 page.
Finger, P. J. et al., Making snack food, British Patent Application GB 2 270 613 A, 1992, Abstract, 1 page.
Taufiq, F., High protein pasta, (fortified with calcium-caseinate and whey), United States Patent US 4,361,591, Abstract, 1 page.
Grindstaff, D. A. et al., High protein pasta. (Contains soy protein isolate and whey protein concentrate), United States Patent US 4,120,989, Abstract, 1 page.
Akin, C. et al., High-protein pasta, Untied States Patent US 3,968,258, Abstract, 1 page.
Murthy, P. R., High protein pasta, United States Patent US 3,949,101, Abstract, 1 page.
Marsland, C. H., Novel food material technology with controllable functional characteristics and industrial process applications, and the resulting fabricated foods, United States Patent Application Publication US 2003/0091698 A1, 2003, Abstract, 1 page.
Orlando, C., Soy-based pasta, United States Patent Application Publication US 2002/0155206 A1, 2002, Abstract, 1 page.
Permesso AG, [Method for the manufacture of carbohydrate-reduced, protein-enriched pasta products.] Verfahren zur Herstellung kohiehydratarmer Teigwaren, die mit Eiweissen angereichert sind, Swiss Patent CH 531 838, 1973, Abstract, 1 page.
Zohoungbogbo, M.C., Dietetic food composition and dietetic method using such composition, United States Patent US 6,569,483 B, 2001, Abstract, 1 page.
Zohoungbogbo, M.C. et al., Pharmaceutical composition for treating side-effects of a diet with reduced amounts of carbohydrates, European Patent Application EP 0 965 351 A2, 1999, Abstract, 1 page.
Zohoungbogbo, M.C. et al., Dietetic food composition and dietetic method using such composition, European Patent Application EP 0 965 278 A1, 1998, Abstract, 1 page.
Xiong, Jungong, Use of hybrid *Rumex acetosa* L. in production of wheat flour-containing product, PCT International Patent Application WO 99/57984 A1, 1999, Abstract, 1 page.
Hsu, J. Y., Preparation of vegetable pastas, United States Patent US 4,517,215, 1985, Abstract, 1 page.
Hsu, J. Y., Preparation of vegetable pastas, United Kingdom Patent Application GB 2 141 315 A, 1984, Abstract, 1 page.
Kristiansen, B. et al., Process for making pasta filata type cheese, United States Patent US 4,460,609, 1984, Abstract, 1 page.
Taufiq, F., High protein pasta product, United States Patent US 4,361,591, 1982, Abstract, 1 page.
Taufiq, F., High protein pasta product, United Kingdom Patent Application GB 2 079 287 A, 1982, Abstract, 1 page.
Miyatake, T., [Rice noodles], Japanese Examined Patent JP 5617059, 1981, Abstract, 1 page.
Grindstaff, D. A. et al., High protein pasta formulation, United States Patent US 4,120,989, 1978, Abstract, 1 page.
Akin, C., High protein pasta, United States Patent US 3,968,258, 1976, Abstract, 1 page.
Murthy, P. R., High protein pasta, United States Patent US 3,949,101, 1976, Abstract, 1 page.

(Continued)

*Primary Examiner* — Lien T Tran

(74) *Attorney, Agent, or Firm* — Fitch, Even, Tabin & Flannery LLP

(57) ABSTRACT

The invention provides for the use of a texture modifying agent added to nutritionally enhanced pasta dough, such as pasta dough with high levels of protein, so that a pasta product can be produced with a quality similar to that of conventional pasta. The texture modifying agent, which preferably includes an enzyme, permits the nutritionally enhanced pasta dough to be extruded in conventional pasta manufacturing equipment and to form a pasta product with a texture similar to typical semolina-based pasta.

4 Claims, No Drawings

(56) References Cited

OTHER PUBLICATIONS

Scharschmidt, R. K. et al., High protein pasta, United States Patent US 3,615,677, 1971, Abstract, 1 page.

Decke, L., [Farinaceous products for diabetics and production process] Diabetiker-Teigwaren and Verfahren zu deren Herstellung, West German Patent Application DE 1 900 197, 1971, Abstract, 1 page.

Pates Alimentaires Rivoire et Carret, High aleurone pasta, British Patent GB 1 182 510, 1970, Abstract, 1 page.

Gualandi, P. et al., High protein content pasta and energy-restricted food preparation including said pasta, PCT Patent Application WO 01/64056 A1, 2001, Abstract, 1 page.

Zohoungbogbo, M. C., Dietetic food composition and dietetic method using such composition, United States Patent US 6,322,826 B, 1999, Abstract, 1 page.

* cited by examiner

NUTRITIONALLY ENHANCED PASTA

CROSS-REFERENCE TO RELATED APPLICATION

This application is a divisional of prior application Ser. No. 11/319,149 filed Dec. 27, 2005 Now Abandon, which is hereby incorporated herein by reference in its entirety.

FIELD OF THE INVENTION

The invention relates to nutritionally enhanced pasta, and more particularly, to pasta with increased protein levels which maintains the organoleptic characteristics of conventional pasta.

BACKGROUND OF THE INVENTION

The nutritional quality of pasta, and often its taste and texture, generally depend upon the flour used to form the pasta. For instance, pasta made with whole grain flours, such as whole wheat pasta, is nutrient-rich because it contains bran and germ. However, the whole grain flour pasta generally does not have the textural characteristics desired by the consumer and its dough is difficult to process into the desired pasta shapes. Pasta formulas containing large amounts of protein, such as 20 percent or more, make the pasta dough hard to extrude and produces a product exhibiting rubbery characteristics or an extremely firm texture.

Most pasta, as a result, is made with durum wheat, which is hard wheat with increased levels of highly functional protein (gluten). Typically flours used to produce pasta have about 10 to about 13 percent protein. Durum wheat is desired for pasta because it makes dough that sticks together well and holds its shape, which are features preferred for pasta manufacture. More importantly, the durum wheat flour also produces pasta having a textural characteristic desired by the consumers—a firm, yet chewy pasta generally characterized as "al dente." Most high quality pasta is made with durum wheat semolina, which is a more coarsely ground wheat flour. However, in these flours, the germ and bran have been removed and, therefore, the fiber and nutritional values are generally lower than the whole grain flours.

In today's weight- and health-conscience society, high protein and low carbohydrate foods are often desired as part of a modified diet that may result in weight loss. As a result, attempts have been made to modify traditional foods with higher levels of protein and lower levels of carbohydrates to satisfy this consumer demand. However, such food reformulation is often difficult because, while the reformulated food may have higher levels of protein and lower levels of carbohydrates, it may not have the mouthfeel or organoleptic properties of conventional food. To achieve consumer acceptance of the nutritionally enhanced products, it is preferred to achieve textural, mouthfeel, and organoleptic properties similar to the conventional foods they are replacing.

Formulating nutritionally enhanced pasta, such as high-protein and low-carbohydrate pasta, is no exception. Increasing the protein levels in pasta, either through fortification with other sources of protein (i.e., soy protein, wheat gluten, or dairy proteins) or by using higher protein flours, is wrought with difficulties. Prior attempts at producing a high protein, low carbohydrate pasta through the selection of specific ingredients generally produces pasta that exhibits chewy and rubbery mouthfeel characteristics, which are not typically desired by the consumer.

Moreover, high levels of highly functional protein (i.e., levels greater than about 13 percent in the raw materials) in pasta dough are also difficult to process. Protein sources such as gluten, wheat protein isolates, and soy protein isolates, when used to manufacture pasta dough, would fall in this difficult-to-process category. For instance, such high levels of protein in pasta dough are often more difficult to extrude, particularly at very high levels of incorporation, such as levels greater than about 18 to about 20 percent protein in the dough. During pasta manufacture, gluten in pasta dough absorbs water and swells to form a cross-linked network, which is typically referred to as gluten development. However, higher levels of gluten in pasta dough absorb higher levels of water that can result in a rapid and extensive gluten development to form pasta dough that is highly elastic, and which has a tendency to exhibit a property called "balling" during processing. Highly elastic pasta dough is very difficult to process using extruders. For instance, very elastic dough obtained through strong protein-protein interactions will result in high press pressures and will be hard to process. Moreover, the dough will also have a tendency to ball or adhere to the paddles or other surfaces of the mixer. Furthermore, if the material has a strong tendency to ball, such material will not feed properly from the blender into the press, causing intermittent flow with associated defective product or creating extremely high pressures at the press with problems in process control.

On the other hand, fortifying pasta dough with other low functionality proteins or using alternative flours to increase the protein levels in the pasta also does not form a satisfactory product. For example, pasta dough has previously been processed with dairy or whey proteins and/or corn, rice, or soy flour to achieve high protein pasta. However, these protein sources generally have poor network forming characteristics and, therefore, do not create desirable pasta. Levels of these low functionality proteins, especially above about 5 percent, typically form dough that does not produce the desired texture of a semolina product because of poor ability to create a strong protein network.

Accordingly, there is a desire for nutritionally enhanced pasta with increased protein levels that can be processed through traditional pasta manufacturing equipment that also exhibits textural, mouthfeel, and organoleptic properties of conventional pasta.

SUMMARY OF THE INVENTION

The invention relates to nutritionally enhanced pasta dough and a method of manufacture thereof to form a nutritionally enhanced pasta product that has a texture similar to semolina-based pasta. Moreover, the nutritionally enhanced pasta dough described herein can also be extruded through conventional pasta manufacturing equipment with minimal or no alterations from the conditions used to manufacture conventional pasta dough. That is, the nutritionally enhanced pasta dough has an elasticity such that it exhibits an extruder or press pressure similar to that of a conventional pasta dough.

Preferably, the nutritionally enhanced pasta dough has a protein source in an amount such that the nutritionally-enhanced pasta product has greater than about 13 percent protein, and most preferably, about 20 to about 35 percent protein. For instance, the nutritionally enhanced pasta dough includes high levels of wheat flour, vital gluten, wheat protein isolates, soy protein isolates, or combinations thereof to achieve the protein enhancement. While conventional pasta dough having high levels of such proteins typically has an undesirable texture and/or is difficult to extrude, it has been discovered that the addition of a texture modifying agent to the pasta dough modifies the elasticity of the dough to enable conventional extrusion and forms a product having a texture similar to a more conventional, semolina-based pasta product.

In one form, the texture modifying agent includes an enzyme, preferably a proteolytic enzyme, in an amount sufficient to provide the desired texture and elasticity. Preferably, the texture modifying agent includes about 50 to about 500 ppm of the proteolytic enzyme in the dough, which may be endo-peptidases, exo-peptidases, or mixtures thereof. In particular, it has been discovered that papain, bromelain, proteases of microbial origin, or combinations thereof provide the desirable characteristics (i.e., semolina-like texture and extrudability) even to a pasta dough having about 30 to about 35 percent protein.

Optionally, the texture modifying agent also includes a reducing agent. While not wishing to be limited by theory, it is believed that the inclusion of a reducing agent relaxes the dough by inhibiting the formation of protein-protein interactions that might form a stronger protein network, which would create a rubbery texture and an elasticity unsuitable for extrusion. If included in the formula, it is preferred that the dough contain about 50 to about 200 ppm of the reducing agent. Preferable reducing agents are ascorbic acid, L-cysteine, sorbic acid, fumaric acid, or mixtures thereof.

Optionally, the texture modifying agent may further include other dough modifiers that also interfere with the formation of protein-protein interactions. For instance, the texture modifying agent may include about 5,000 to about 20,000 ppm (i.e., about 0.5 to about 2.0 percent) of glyceryl monoestearate, mono- and di-glycerides, or mixtures thereof in the dough.

The nutritionally enhanced pasta dough of the prevent invention can be processed through conventional pasta manufacturing equipment. To ensure adequate blending of the texture modifying agent, it is preferred that the texture modifying agent be mixed with the process water prior to blending with the remaining ingredients. However, it has been discovered that the nutritionally enhanced pasta dough can be blended and extruded with less water than conventional pasta dough under similar processing conditions. For example, it has been discovered that by adding the texture modifying agent, as described above, about 20 to about 30 percent less water can be used in the manufacturing process.

DESCRIPTION OF THE PREFERRED EMBODIMENTS

In general, the invention provides for the use of a texture modifying agent added to nutritionally enhanced pasta dough so that the dough can be processed through common pasta manufacturing equipment and exhibit characteristics similar to those of conventional pasta. The nutritionally-enhanced pasta dough [hereinafter dough or pasta dough] is formed from whole grain, multigrain, high protein sources, low carbohydrate sources, reduced carbohydrate sources as well as mixtures thereof to provide pasta dough having levels of protein greater than traditional pasta dough. Even with high levels of protein, the texture-modifying agent permits the nutritionally enhanced pasta dough to be extruded in conventional pasta manufacturing equipment and to form a pasta product with a texture similar to typical semolina-based pasta. For purposes of this invention, conventional, typical, or semolina-based pasta is pasta formed from durum wheat having less than or equal to about 13 percent protein that exhibits a firm and chewy pasta characterized as "al dente."

The nutritionally enhanced pasta dough includes a protein source such that the dough forms a pasta product having levels of protein greater than about 13 percent. Preferably, the dough include a source of gluten, such as wheat flour, vital gluten, wheat protein isolates, soy protein isolates, or combinations thereof, in an amount so that the pasta product has greater than about 13 percent protein and, more preferably, about 20 to about 35 percent protein. Conventional high protein pasta dough with these protein levels, while nutritionally preferred because of the increased levels of protein, typically forms a pasta product that is tough and rubbery and often not desired by the consumer. Moreover, due to rapid and excessive gluten development during processing, such conventional pasta dough is also difficult to extrude using traditional extrusion techniques. As a result, in order to obtain the desired textural and processing qualities with pasta dough having such high levels of protein, the texture modifying agent is added to the pasta dough.

In one form, the texture-modifying agent is an enzyme, preferably a proteolytic enzyme (i.e., an enzyme having protease activity). Preferably, the enzyme is papain, bromelain, proteases of microbial origin, and combinations thereof. Most preferably, the proteases of microbial origin are derived from *Aspergillus Orizae*.

While not wishing to be limited by theory, it is believed that enzymes with endo- or exo-peptidase activity, such as papain, bromelain or the like, can hydrolyze or break peptide bonds in protein and polypeptides to achieve dough elasticity suitable for extrusion and a texture comparable to conventional pasta. In addition, it has been discovered that microbial proteases derived from *Aspergillus Orizae* can be used to reduce the extent of gluten development and the level of protein network formation in the finished dry pasta product.

Again, while not wishing to be limited by theory, it is believed that the enzymes minimize gluten development by breaking peptide bonds and cleaving amino acid groups from the protein and polypeptide chains. As a result, protein-protein interactions and other reactions with the proteins are reduced and perhaps even minimized. Accordingly, depending on whether internal or external bonds are to be hydrolyzed, enzyme blends may be utilized to achieve various processing or final product characteristics.

Many factors determine whether an enzyme is suitable as the texture-modifying agent. For example, the level of enzyme addition, the characteristics of the particular enzyme, the specific activity of the enzyme (i.e., endo- or exo-peptidase activity, and the like), and the type of protein used in the formula are all factors that may affect whether or not the specific enzyme can function as the texture-modifying agent. In general, however, the higher the protein level, the higher the level of enzyme required, and vice versa. At a minimum, a particular enzyme is suitable for the texture-modifying agent if the enzyme provides the pasta dough with a rheology suitable for extrusion through conventional pasta manufacturing equipment (i.e., as described below) and forms a pasta product having a texture of typical semolina-based products.

Depending on protein levels, enzyme amounts ranging from about 50 to about 500 ppm in the dough are generally suitable for use as the texture-modifying agent. As illustrated below, the preferred level of enzyme within this range will also generally vary depending on enzyme activity and specificity.

For example, with protein levels of about 30 to about 35 percent, protease levels in the dough of about 300 to about 500 ppm of *Aspergillus Orizae* are preferred to provide extrudability and the desired pasta texture. Protease amounts above this level, however, will often result in very soft, elastic, sticky dough, which is considered to be undesirable.

Enzymes with exo- and endo-peptidase activity generally require smaller concentrations of the enzyme to achieve desirable results. For example, in a pasta dough having protein levels around about 30 percent, about 200 to about 400 ppm of such enzymes in the dough are preferred to provide extrudability and the desired texture.

On the other hand, enzymes with only exo-peptidase activity generally require higher concentrations of the enzyme to achieve desired results. For instance, in pasta dough also having protein levels around about 30 percent, about 400 to about 500 ppm of enzymes with only exo-peptidase activity are preferred to achieve desired pasta texture and extrudability.

Enzymes with only endo-peptidase activity, on the other hand, also require less enzyme addition. Preferably, about 100 to about 200 ppm of papain or bromelain are suitable as the texture-modifying agent with pasta dough having between about 30 to about 35 percent protein. Higher levels of these enzymes resulted in an undesirable pasta. For instance, adding between about 400 to about 500 ppm of bromelain or papain to a pasta with similar protein levels of gluten resulted in soft mushy pasta. Again, not wishing to be limited by theory, it is believed that because the enzymes with only endo-peptidase activity hydrolyze the peptide bonds within the protein structure to divide the protein chain into smaller polypeptides, that high levels of these enzymes break up the proteins into such small structures that a weak protein network is formed which is too soft and elastic.

In other forms, the texture-modifying agent includes both a proteolytic enzyme, as discussed above, and a reducing agent. The inclusion of a reducing agent along with the enzyme can further modify the elastic and processing characteristics of the high-protein dough. It is believed that the reducing agent helps relax the dough so that protein-protein interactions are inhibited. Preferably, the reducing agent is ascorbic acid, L-cysteine, sorbic acid, fumaric acid, and the like, or combinations thereof. Similar to the enzyme levels discussed above, the higher the protein level, the higher the level of reducing agent is generally required.

For example, about 50 to about 200 ppm in the dough of ascorbic acid, in conjunction with the aforementioned enzymes, produces improvement in dough performance (i.e., improved extrudability) and finished product characteristics (i.e., texture similar to a semolina-based product). In general, when using reducing agents such as ascorbic acid or L-cysteine in combination with an enzyme, lower levels of the aforementioned proteases were found to be preferable.

Ascorbic acid, in particular, was found to be effective in modifying the characteristics of the dough and the dry pasta when used in conjunction with enzymes containing endo- and exo-peptidase activity. For example, at about 100 to about 200 ppm of ascorbic acid in the dough in conjunction with enzymes with exo- and endo-peptidase activity (i.e., about 200 to about 400 ppm), acceptable modification of the elastic properties of the pasta dough is observed so that the dough can be processed in a conventional manner (i.e., using conventional extruder techniques and equipment). That is, a decrease in the operating press pressure by about 10 to about 15 percent as compared with the pressure when the enzyme was used without the ascorbic acid is observed. As will be further discussed below, measurement of extruder or press pressure is one method of determining acceptable dough elasticity properties of the dough. At this level of dough modifiers, decreases in water requirements for the process were also observed (i.e., about 25 to about 30 percent).

With regard to the use of L-cysteine hydrochloride as a reducing agent, a positive change of the elastic characteristics of the pasta dough was also achieved. For instance, concentrations in the range of about 50 to about 200 ppm of L-cysteine hydrochloride in the dough were found to provide acceptable results, depending on the enzyme used and level of protein in the dough. In general, however, it is preferred that the texture modifying agent include protease and L-cysteine combinations as compared with protease or ascorbic acid, alone or in combination, at the same levels of addition, due to less extensive softening of the finished product.

In yet another form, the texture-modifying agent includes a proteolytic enzyme and/or a reducing agent together with other dough modifiers, such as glyceryl monoestearate, other mono- and di-glycerides, and the like. The addition of other dough modifiers along with the enzyme and/or reducing agent can further improve the processability of high-protein dough. While not wishing to be limited by theory, it is believed that the addition of the dough modifiers minimizes the amount of shear in the product, which decreases the protein reactivity, and also interferes with protein-protein interactions. Compounds such as glyceryl monoestearate provide lubricity to the system, thus modifying the flowability of the dough and lowering shear levels in the system. As a result, the dough is further softened.

For instance, the pasta dough may optionally include about 0.5 to about 2 percent of the dough modifier (i.e., about 5,000 to about 20,000 ppm). Addition of the dough modifier further interferes with protein network formation and thus, enzyme and/or reducing agent levels can generally be decreased. Lower levels of gluten development or decreased protein-protein interactions due to interference in the system or a decrease in the amount of work necessary to prepare the dough will result in a softer dough and lower texture development in the finished product. Moreover, glyceryl monoestearate interacts with the amylose fraction of the starch in the pasta formula minimizing starch damage during the process and in general rounding up the texture characteristics of the pasta.

One method for determining acceptable elasticity or rheological characteristics of the nutritionally enhanced dough is through the measurement of pressure in the extruder or press during manufacture of the pasta shapes. It is preferred that the texture modifying agent modify the rheological properties of the dough such that it can be processed in a manner and with an extruder pressure consistent with a conventional pasta dough. For instance, a high protein and reduced carbohydrate formula dough generally has acceptable rheological characteristics if the operating pressure is about 90 to about 95 bars when manufacturing penne using 460 mm dies in a 4,000 lb/hr press. In this situation, once pressures climb outside this range, process control and ability to maintain good product quality becomes more difficult. However, the press pressure may also vary depending on the pasta shape desired.

In one form, the nutritionally-enhanced pasta dough will include about 30 percent or more of whole wheat flour (preferably about 30 to about 60 percent), about 5 to about 15 percent of wheat protein isolate, about 5 to about 15 percent vital gluten, about 10 to about 30 percent of a modified wheat starch, 0 to about 2 percent of a dough modifier such as glyceryl monoestearate (preferably about 0.5 to about 2 percent), 0 to about 200 ppm of a reducing agent, and about 50 to about 500 ppm of an enzyme.

Preferably, the dough includes a combination of enzymes with endo- and exo-peptidase activity together with glycerol monoestearate as the dough modifier. Most preferably, the dough includes a combination of enzymes with endo- and exo-peptidase activity together with the reducing agent and glyceryl monoestearate.

For instance, it is most preferred to incorporate a protease with endo- and exo-peptidase activity at about 300 to about 400 ppm, the reducing agent L-cysteine at about 50 to about 100 ppm, and glyceryl monoestearate at about 0.75 to about 1.5 percent into dough having a gluten level of about 25 to about 35 percent.

The preferred combinations of enzyme and reducing agent, as well as levels of addition, will often vary depending on the pasta formula, particularly on the type and level of protein (i.e., gluten or the like). Due to its strong tendency for protein-protein interaction, formulations containing highly functional gluten require higher protease and/or reducing agent levels as discussed above. On the other hand, formulas containing soy protein appear to require lower protease levels, due to a less firm protein matrix as a result of a less functional protein.

For instance, a proper balance of the components of the texture modifying agent is another factor that affects the pasta product. For instance, very high enzyme levels (i.e., about 400 to about 500 ppm), particularly for proteases with endo-peptidase activity in conjunction with high levels of reducing agents (i.e., about 50 to about 100 ppm or higher), produces a dough with undesirable elastic material when the gluten levels are about 25 to about 35 percent. A decrease in the operating pressure at the press was observed, however, when using such extremes. It was observed that the operating pressure was lowering by about 15 to about 25 percent.

The nutritionally enhanced pasta dough with the texture-modifying agent can be processed through conventional pasta making equipment. However, it has also been discovered that the level of enzyme addition may vary depending on the specific type of equipment used, largely because the residence time in the apparatus will determine the time allowed for enzymatic action. For instance, the residence time of the dough in the mixer or other equipment, will affect the amount of enzyme addition since this determines the time the enzyme will act on the dough.

Preferably, the texture modifying agent, such as the enzyme, is first added to the process water to form a water pre-mix solution. This water pre-mix solution is then added to a blender along with the other ingredients to form the dough. In this manner, the enzyme will be sufficiently mixed with the remaining ingredients. The time allowed for enzymatic action, therefore, will include the residence time of the material in the blender, the residence time of the material in the press or extruder, and the residence time in any ducts therebetween. Accordingly, the level of enzyme addition should be varied depending on the size of the blender and press as well as the diameter and length of any ducts that transfer the dough from the blender to the extruder. Enzyme inactivation will take place, once the pasta enters the shaker/pre-dryer, where the material is exposed to high temperatures and humidity.

The same approach applies to the addition of the reducing agents and/or other dough modifiers. For instance, if ascorbic acid is to be added as part of the formula, ascorbic acid preferably should be solubilized in the process water to increase its reactivity in the system. It is expected that the reactivity of the reducing agent will decline as the pasta moisture content decreases going through the pasta driers.

With addition of the texture-modifying agent to the dough, water requirements for the process were also found to change over conventional pasta manufacture. That is, under process conditions that would create highly elastic and stretchable dough (i.e., high levels of protein), it was also discovered that less water than with conventional pasta dough could be used if the texture-modifying agent is added to the dough. For example, about 25 to about 30 percent less water may be incorporated into the process when using the texture modifying agent. Excess water may result in dough with a tendency to adhere to the paddles of the mixer and balling.

However, the water levels and texture modifying amounts need to be balanced to permit both good extrudability and formation of desired pasta. For example, even with about 25 to about 30 percent less water in a formula containing about 30 to about 35 percent protein and about 400 to about 500 ppm of enzymes (with strong endo-peptidase activity) in conjunction with about 150 to about 300 ppm of reducing agents, such as ascorbic acid, did not form a good finished product. Such formulation is extrudable; however, it produces undesirable soft pasta, which is believed to be a result of the high amounts of the endo-peptidase enzymes.

Accordingly, by controlling the water addition, proper consistency of the dough can be achieved along with the proper addition of the texture-modifying agent. As discussed above, pressure at the press was found to be a good indication of the proper enzyme and reducing agent levels. Therefore, in the example of the previous paragraph, reduction in the levels of enzyme and reducing agent to about half of their levels in combination with the proper water amounts, would prevent problems with extremely elastic characteristics to form an extrudable and firm pasta.

Pasta products produced from the nutritionally-enhanced pasta dough were evaluated through a texture analyzer, such as Instron and FTC press, as well as through sensory evaluations via taste tests. The most preferred texture profiles were obtained when enzymes with endo- and exo-peptidase activity were processed in the presence of L-cysteine and glyceryl monoestearate, followed by samples containing this protease and glyceryl monoestearate. In general, samples using the same enzyme but with ascorbic acid, were softer and less desirable in texture quality that samples using L-cysteine. Thus, although the dough was generally easier to process with the enzyme and ascorbic acid as the texture modifying agent, the overall effect in pasta quality was not as desirable.

The Examples that follow are intended to illustrate, and not to limit, the invention. All percentages used herein are by weight, unless otherwise indicated.

EXAMPLE 1

This example evaluated pasta dough prepared using a texture modifying agent of a microbial protease enzyme with endo- and exo-peptidase activity together with L-cysteine and glyceryl monoestearate.

TABLE 1

| Formulation | |
| --- | --- |
| Ingredient | Amount |
| Whole wheat flour | 52% |
| Wheat protein isolate | 12% |
| Vital Wheat gluten | 12% |
| Modified starch | 22.95% |
| Microbial protease (endo- and exo-peptidase) | 350 ppm |
| L-Cysteine | 100 ppm |
| Glyceryl monoestearate | 1% |

The ingredients of Table 1 were blended together with about 27 percent water to form a dough. The dough was extruded through a press at a pressure of about 80 bars. The process generally had a residence or reaction time of around 12 minutes for the texture modifying agent. The resultant pasta contained about 27 percent protein.

The formed pasta had an excellent quality with a texture similar to that of semolina-based products. A panel of taste testers indicated the pasta was not rubbery, had a proper texture balance and firmness as compared to semolina products, was not soft or mushy, and had no tooth-packing characteristics.

EXAMPLE 2

This example evaluated pasta dough prepared using a texture modifying agent of a microbial protease enzyme with endo- and exo-peptidase activity together with L-cysteine.

TABLE 2

| Formulation | |
|---|---|
| Ingredient | Amount |
| Whole wheat flour | 52% |
| Wheat protein isolate | 12% |
| Vital Wheat gluten | 12% |
| Modified starch | 22.96% |
| Microbial protease (endo- and exo- peptidase) | 350 ppm |
| Glyceryl monoestearate | 1% |

The ingredients of Table 2 were blended together with about 34 percent water to form a dough. The dough was extruded through a press at a pressure of about 100 bars. The process generally had a residence or reaction time of around 12 minutes for the texture modifying agent. The resultant pasta contained about 27 percent protein.

The process formed a product having excellent quality with a texture similar to that of semolina-based products. While acceptable, the overall texture profile was not as desirable as the product described above in Example 1. As described by a sensory panel, the pasta was not rubbery, had a proper texture balance, had proper firmness as compared to semolina products, was not soft or mushy and had no tooth-packing characteristics.

It will be understood that various changes in the details, materials, and arrangements of formulations and ingredients, which have been herein described and illustrated in order to explain the nature of the invention may be made by those skilled in the art within the principle and scope of the invention as expressed in the appended claims.

What is claimed is:

1. A method of extruding a pasta product having about 20 to about 35 percent protein, the method comprising:
    adding a texture-modifying agent including about 50 to about 500 ppm of an enzyme having peptidase activity consisting of endopeptidase activity, the enzyme selected from the group consisting of papain, bromelain, proteases of microbial origin derived from *Aspergillus Orizae*, and combinations thereof, about 50 to about 200 ppm of a reducing agent selected from the group consisting of ascorbic acid, L-cysteine, sorbic acid, fumaric acid, and combinations thereof, and about 5,000 to about 20,000 ppm of a dough modifier selected from the group consisting of glyceryl monoestearate, monoglycerides, diglycerides, and combinations thereof into water to form a water pre-mix;
    blending the water pre-mix into a pasta dough having wheat flour and an additional protein source selected from the group consisting of wheat flour, vital gluten, wheat protein isolates, soy protein isolates, and combinations thereof in an amount such that the pasta product has about 20 to about 35 percent protein wherein the amount of water is about 1 time that of the amount of protein in the pasta dough or wherein the amount of water is about 1.3 times that of the amount of protein in the pasta dough;
    extruding the pasta dough through a die orifice into the pasta product; and
    wherein the texture modifying agent and amount of water relative to the amount of protein allows the pasta dough having about 20 to about 35 percent protein to be extruded through the die orifice and provide an al dente texture of a semolina-based pasta product having about 10 to about 13 percent protein.

2. The method of claim 1, wherein the pasta dough comprises about 30 to about 60 percent wheat flour; about 5 to about 15 percent wheat protein isolate; and about 5 to about 15 percent vital gluten.

3. A method of extruding a pasta product having 27 to about 35 percent protein, the method comprising:
    adding a texture-modifying agent including about 50 to about 500 ppm of an enzyme having peptidase activity consisting of endopeptidase activity, the enzyme selected from the group consisting of papain, bromelain, proteases of microbial origin derived from *Aspergillus Orizae*, and combinations thereof, about 50 to about 200 ppm of a reducing agent selected from the group consisting of ascorbic acid, L-cysteine, sorbic acid, fumaric acid, and combinations thereof, and about 5,000 to about 20,000 ppm of a dough modifier selected from the group consisting of glyceryl monoestearate, monoglycerides, diglycerides, and combinations thereof into water to form a water pre-mix;
    blending the water pre-mix into a pasta dough having wheat flour and an additional protein source selected from the group consisting of wheat flour, vital gluten, wheat protein isolates, soy protein isolates, and combinations thereof in an amount such that the pasta product has 27 to about 35 percent protein wherein the amount of water is about 1 time that of the amount of protein in the pasta dough or wherein the amount of water is about 1.3 times that of the amount of protein in the pasta dough;
    extruding the pasta dough through a die orifice into the pasta product; and
    wherein the texture modifying agent and amount of water relative to the amount of protein allows the pasta dough having 27 to about 35 percent protein to be extruded through the die orifice and provide an al dente texture of a semolina-based pasta product having about 10 to about 13 percent protein.

4. The method of claim 3, wherein the pasta dough comprises about 30 to about 60 percent wheat flour; about 5 to about 15 percent wheat protein isolate; and about 5 to about 15 percent vital gluten.

* * * * *